United States Patent [19]

Freeman et al.

[11] Patent Number: 4,839,516

[45] Date of Patent: Jun. 13, 1989

[54] METHOD FOR QUANTITATIVE ANALYSIS OF CORE SAMPLES

[75] Inventors: David L. Freeman, Garland, Tex.; Mark G. Rockley, Stillwater, Okla.; Donald G. Harville, Grapevine, Tex.

[73] Assignee: Western Atlas International, Inc., Houston, Tex.

[21] Appl. No.: 118,156

[22] Filed: Nov. 6, 1987

[51] Int. Cl.$^4$ .............................................. G01N 21/85
[52] U.S. Cl. .................................. 250/255; 250/253; 250/339; 250/341
[58] Field of Search ............... 250/255, 253, 341, 340, 250/339; 436/31, 25, 174, 171

[56] References Cited

U.S. PATENT DOCUMENTS 4,321,465 3/1982 Stover et al. ........................ 250/255

OTHER PUBLICATIONS

Pierre L. Robin and Paul G. Rouxhet, "Contribution of Molecular Water in the Infrared Spectra of Kerogens and Coals" Fuel, vol. 55 (July 1976) pp. 177-183.

Tuddenham et al., "Infrared Techniques in the Identification and Measurement of Minerals", Analytical Chemistry, Nov. 1960.

Fridmann, "Pelleting Techniques in Infrared Analysis", *Progress in Infrared Spectroscopy* No. 3, pp. 1-23, 1967.

Estep, et al., "Quantitative Infrared Multicomponent Determination of Minerals Occurring in Coal", Analytical Chemistry, Feb. 1968.

Fripiat, "Application of Far Infrared Spectroscopy to the Study of Clay Minerals and Zeolites", *Advanced Techniques for Clay Mineral Analysis Elsevier*, 1982.

"The McCrone Micronizing Mill and Sample Preparation Kit", Brochure, McCrone Research Associates, Ltd.

Hunt, "Infrared Spectral Behavior of Fine Particulate Solids", Journal of Physical Chemistry, 1976.

Duyckaerts, "The Infrared Analysis of Solid Substances" Nov., 1958, *The Analyst*, vol. 84, pp. 201-214.

Dachille et al., "High Pressure Phase Transformations in Laboratory Mechanical Mixers and Mortars", NATURE, Apr. 1960.

Morris, "Infrared Spectrophotometric Analysis of Calcium Sulfate Hydrates", Analytical Chemistry, Sep. 1963.

Hunt et al., "Visible and Near Infrared Spectra of Minerals and Rocks: XII Metamorphic Rocks", MODERN GEOLOGY, 1976.

Hunt, et al., "Visible and Near Infrared Spectra of Minerals and Rocks: XI Sedimentary Rocks" MODERN GEOLOGY, 1976.

Hunt, "Spectral Signatures of Particulate Minerals in the Visible and Near Infrared" GEOPHYSICS, Apr. 1977.

Hunt, "Spectra of Altered Rocks in the Visible and Near Infrared", ECONOMIC GEOLOGY, 1979.

Wilson, "A Handbook of Determination Methods in Clay Mineralogy", pp. 133-173, 1987.

*Primary Examiner*—Janice A. Howell
*Assistant Examiner*—Constantine Hannaher
*Attorney, Agent, or Firm*—Robert E. Lowe; E. Eugene Thigpen; Barry C. Kane

[57] ABSTRACT

A method for quantitative mineral analysis of core samples obtained from oil and gas wells is disclosed. The method includes the steps of grinding the sample to very small particle size and combining the sample with a carrier material such as KBr to form a pellet. The pellet is observed in a Fourier transform infra-red spectrometer and the resultant spectra compared with those of known standards in a digital computer to produce a quantitative analysis of the material.

13 Claims, No Drawings

METHOD FOR QUANTITATIVE ANALYSIS OF CORE SAMPLES

BACKGROUND OF THE INVENTION

This invention relates to the field of quantitative analysis of earth samples, particularly to earth samples of the kind typically obtained in the process of exploration for or production of oil and gas. As oil and gas wells are drilled, it is common practice to obtain samples of the earth at different depths of interest in the well, such samples being generally termed core samples in the industry. Core samples are subjected to numerous tests and analyses in an effort to learn as much as possible about the makeup and characteristics of the earth formations in the zones of interest.

One of the items of interest concerning core samples that is of great interest to geologists is the mineral content of the sample. Knowledge of the mineral content yields valuable information in classifying the type and characteristics of the earth layer in question. In this regard it is vital for the geologist to know not only which particular minerals are present, but in what quantities, or proportions.

In the past, quantitative analysis of core samples have been a time consuming and expensive process. The technique most commonly used in the industry has been x-ray diffraction analysis or "XRD" XRD is for the most part capable of yielding satisfactory results when carried out by highly trained personnel. However, the method is time consuming, requiring from several hours to days to complete, and is correspondingly expensive. Therefore, there has long been a need in the oil and gas industry for a rapid, inexpensive method of making a quantitative determination of the mineral composition of core samples. This invention fulfills that long felt need.

SUMMARY OF THE INVENTION

The present invention discloses a method whereby Fourier-transform infra-red spectroscopy may be employed to obtain quantitative mineral analysis of core samples. Samples of core materials are prepared in accordance with the steps of the method and the infra-red response of the sample is determined. The response is compared to the responses of known minerals to determine the quantities of each mineral component in the sample.

DESCRIPTION OF PREFERRED EMBODIMENTS

Although not limited thereto, the invention is chiefly directed to the analysis of core samples obtained from the earth in connection with oil and gas exploration and production. Such samples are taken from boreholes in the earth, and may be taken from oil or gas producing formations or from exploratory wells which have not yet produced oil or gas. Depending upon the sample gathering technique employed, the core material may be about 3 inches in diameter and perhaps several feet long. Frequently smaller samples are extracted from the larger sample once it has reached the surface, the smaller samples being frequently referred to as "plugs". These plugs are generally about 1 inch or less in diameter and perhaps 1.5–2.0 inches long. Other samples may be obtained from the sidewalls of the borehole, these samples being of a size similar to that of the plugs just described. The analytical techniques described herein may also be applied to drill cuttings, that is, the tailings that result from drilling. Such cuttings are not normally referred to as core samples, but for purposes of brevity, the term core samples as used in this application is intended to include both sidewall core samples and drill cuttings in addition to conventional cores.

The portion of the core sample to be analyzed is cleaned to remove any hydrocarbons that might be present. Various core cleaning methods may be used such as toluene solvent extraction or $CO_2$ cleaning. These cleaning methods are well known in the art and further description of them is not thought to be required.

The next step is to reduce the particle size of the sample until the sample particles are of a uniformly fine size. This can be accomplished by grinding in any manner that will produce the required particle size, which is to obtain an average particle size of less than one micron with no particles larger than 2 microns. We have found that these small particle sizes are essential to accurate results. If the particles are too large, such as larger than about 10 microns, various scattering and diffraction effects occur which may cause extremely broad peaks in the sample spectrum. It is possible to correct for the broad peaks through the use of special software filtering techniques, but the problem can be avoided by using the proper particle size in the sample. We prefer to begin by crushing a few grams of the sample in a mortar and pestle until the largest particle size is less than 500 microns. This pre-grinding step may not be required when the sample is initially unconsolidated such as certain tar sand samples. We then place about one gram of the crushed material in about 5 milliliters of isopropyl alcohol and grind in an agate grinding mill, such as a McCrone Micronising Mill manufactured by McCrone Research Associates, Ltd. of London, England, and grind for approximately 15–25 minutes, preferably about 20 minutes. Fluids other than isopropyl alcohol can be used, including water, but the alcohol is preferred. Its viscosity aids in allowing the material to cling to the agate rollers for better grinding, and its volatility shortens the time required to drive it out of the material after grinding.

At the completion of grinding the sample the liquid is poured into a watch glass and dried in a vent hood until all of the liquid carrier is evaporated. A small amount of the dried sample, preferably about 1–3 milligrams is placed in a small capsule with approximately one gram of potassium bromide. The capsule is then agitated or shaken to ensure complete mixing of the sample material and the KBr. It has been found that a dental amalgamator is suitable to provide the desired mixing although we prefer to use capsules made from abrasion resistant metal in place of the plastic capsules that are sometimes provided with such equipment. The use of plastic capsules can cause some sample contamination and affect the final results.

The proportion of sample to KBr is chosen in accordance with the sensitivity of the spectrometer utilized. The final sample or pellet will have different absorbance/transmittance values depending upon the concentration of sample material to KBr in the pellet. Preferably the pellet should fall in the range of about 0.3 to 2.0 maximum absorbance units, where 1 absorbance unit equals 10% transmittance and 2 absorbance units equals 1% transmittance; that is, absorbance units are equal to $log_{10}(100/t)$ where t is the percent transmittance.

After mixing, we prefer to place the capsule containing the mixture in a drying oven at about 65° C. to drive off any residual moisture in the material. Depending upon laboratory conditions of humidity and the like, this particular step may not be required but can in some circumstances improve overall results.

Approximately 200 milligrams of the mixed and dried material is weighed out and placed in a pellet preparation device of the type commonly used to prepare samples for infra-red spectrometric work. We prefer o use a pellet press made by Fred S. Carver, Inc. of Menominee Falls, Wis., specifically for preparation of infra-red spectrometer wafers or pellets. The press places the sample material under high pressure in a die and produces a coherent thin wafer like disk, commonly referred to as a pellet, which is sized for the analytical instrument employed. The press is equipped with a KBr die with gas chromatograph fraction collector, available from Spectra-Tek Co., Stamford, Conn. This produces a pellet 13 millimeters in diameter.

The pellet is loaded into an infra-red spectrometer with Fourier transform capability, such as the Infra-red Fourier Transform Spectrometer (FTIR) spectrometer made by Perkin-Elmer Company of Norwalk, Conn. The spectrometer is operated in its usual fashion, which involves directing a coherent infra-red beam about 8 millimeters wide through the sample pellet and capturing the resultant energy spectra, which will of course be determined by the amounts of infra-red energy absorbed and transmitted by the sample within certain wavelengths of interest.

We prefer to collect spectral data in the range of about 5000 wave numbers to about 400 wave numbers, that is, from about 2 microns to about 25 microns in wavelength. The instrument provides a digital output corresponding to the percent transmittance of the pellet sample for each wavelength of interest, where 100% transmittance would indicate a pure KBr sample pellet. Percent transmittance less than 100% at a particular wavelength indicate that the sample pellet has absorbed energy at those wavelengths. The precise wavelengths at which energy is absorbed is dependent upon the material, and therefore the material can be identified by its own spectral pattern. The amplitude or intensity of the signal at particular wavelengths is indicative of quantity.

The spectrometer produces a digitized signal which is provided via a data link to a digital computer, which can be a micro-computer, commonly referred to as a personal computer or PC.

Pure samples of minerals expected to be encountered in this kind of testing are first tested to establish a data base. The characteristic spectra of each pure substance is stored in the memory of the computer. The computer may then compare the wave number spectra and amplitude of unknown materials with those of the known materials in its memory and from such comparison produce a direct read-out of both the qualitative and quantitative makeup of the unknown core sample material.

In order for the method of the present invention to produce accurate quantitative results it is necessary that the comparison of the spectra of the unknown sample with those of pure component materials stored in memory be extremely precise. The need is especially critical when working with more complex mixtures. That is to say, a particular curve or spectra matching technique may be sufficient when only one or two component materials are present, but that technique may not be sufficiently precise when, say, four to six or more materials are present in the same sample. For this and other reasons it has been widely believed by workers in the field that IR spectrometry was not generally capable of yielding valid quantitative results.

We have developed computer programs for use in the process to overcome the limitations of the prior art. With the programs, we first smooth the spectral curve obtained using a third-degree polynomial over an interval of five data points. The program then interrogates the smoothed curve in a twenty-one data point width, shifting one wave number at a time throughout the range of from 5000 wave numbers to 400 wave numbers. Spectral band profiles, positions and intensities are detected by comparing the fourth, fifth and sixth derivatives of the polynomial defining the curve. We have found that this technique yields the degree of precision necessary for the method to produce consistently valid quantitative results.

The efficacy of the present invention will be described further by reference to the following examples. In each example, the core sample was prepared in the lab so that the quantitative makeup of the sample was known. The sample was then analyzed according to the present invention and that result compared to the known sample makeup.

EXAMPLE I

A sample to be tested was prepared by mixing the following materials in the weight percent shown:

| Mineral | Wt. Percent |
| --- | --- |
| Quartz | 63.6 |
| Calcite | 15.2 |
| Dolomite | 15.7 |
| Clay minerals | 5.5 |

About 5 grams of the above core sample material was placed in a mortar and ground with a pestle until the largest particles were less than 0.5 millimeter in diameter. About 1 gram of the material was placed in a McCrone Micronising Mill to which about 5 milliliter of isopropyl alcohol were added. The material was ground for about 20 minutes which was sufficient to reduce the average particle size to less than 1 micron with no particles larger than 2 microns. The resultant sample liquid was poured off into a watch glass and placed under a vent hood for about 20 minutes, at which time the sample had dried to a powder. 1.67 milligrams of the powder was placed into a metal capsule to which about 1 gram of KBr was added and the capsule was shaken in a dental amalgamator for 1 minute. The capsule was placed in a 65° C. oven for about 10 minutes. 200.5 milligrams of the material in the capsule was then placed in a pellet press and pressed into 13 millimeter thin disk. The disk was placed in a Perkin-Elmer Model 1720 FTIR spectrometer, linked to a digital computer into which characteristic pure spectra had been stored in memory. The digital computer produced the following analysis observed for that single pellet so prepared:

| Mineral | Weight Percent |
| --- | --- |
| Quartz | 67.0 |
| Calcite | 14.0 |
| Dolomite | 16.0 |

-continued

| Mineral | Weight Percent |
|---|---|
| Clay minerals | 3.0 |

EXAMPLE II

The known sample was prepared as in Example I but having the makeup shown in the table below. The sample was then prepared for analysis in the same manner as described above, except that 1.56 milligrams of sample was combined with 1.015 grams of KBr and 201.2 milligrams of the mixture was used to produce the 13 millimeter pellet. The following results were obtained:

| Mineral | Weight Percent | |
|---|---|---|
| | Actual | Observed |
| Quartz | 13.4 | 13.0 |
| Plagioclase | 49.9 | 51.0 |
| Microcline | 15.2 | 17.0 |
| Calcite | 15.7 | 12.0 |
| Clay minerals | 5.5 | 7.0 |

EXAMPLE III

The known sample was prepared as in Example I but having the makeup shown in the table below. The sample has then prepared for analysis in the same manner as described in Example I, except that 1.73 milligrams of sample was combined with 1.01 grams of KBr and 201.8 milligrams of the mixture was used to produce the 13 millimeter pellet. The following results were obtained:

| Mineral | Weight Percent | |
|---|---|---|
| | Actual | Observed |
| Quartz | 14.6 | 14.0 |
| Microcline | 26.6 | 27.0 |
| Anhydrite | 34.8 | 36.0 |
| Clay minerals | 24.0 | 22.0 |

EXAMPLE IV

The known sample was prepared as in Example I but having the makeup shown in the table below. The sample was then prepared for analysis in the same manner as described in Example I, except that 1.72 milligrams of sample was combined with 1.028 grams of KBr and 200.8 milligrams of the resulting mixture was used to produce the 13 millimeter pellet. The following results were obtained:

| Mineral | Weight Percent | |
|---|---|---|
| | Actual | Observed |
| Quartz | 18.7 | 18.0 |
| Plagioclase | 21.4 | 25.0 |
| Microcline | 0.0 | 1.0 |
| Calcite | 23.3 | 20.0 |
| Dolomite | 32.5 | 33.0 |
| Clay minerals | 4.1 | 3.0 |

It can be seen that the results obtained using the method of the present invention in each case were within a few percent by weight of the known sample, and in each case produced accuracy acceptable for the geologic and lithologic analysis required in the oil and gas field. The time required in each case was limited to the total time involved in sample preparation, in all cases about 1 hour.

While the steps in the foregoing method have been described in considerable detail, it will be appreciated that such detail is provided for illustrative purposes and for completeness, and is not intended to limit the scope of the invention in any way, which invention is defined by the appended claims.

We claim:

1. A method for determining the mineral composition of the earth in a selected region of a borehole comprising the steps of:
   (a) obtaining a core sample from said selected region of the borehole;
   (b) cleaning said core sample to remove hydrocarbons;
   (c) grinding at least a portion of said core sample to a particle size less than about 2 microns;
   (d) mixing said ground sample portion with a carrier and pressing said mixture into a thin wafer;
   (e) subjecting said thin wafer to infra-red energy in a Fourier transform infra-red spectrometer to obtain the sample spectral response; and
   (f) comparing said sample spectral response with those of known mineral standards in a digital computer to determine the quantitative mineral composition of said core sample.

2. The method of claim 1 wherein said portion of said core sample is ground to an average particle size of less than about 1 micron with no particles larger than about 2 microns.

3. The method of claim 2 wherein said grinding is carried out in a mechanical grinder in the presence of isopropyl alcohol.

4. The method of claim 3 including the step of drying said ground sample portion to remove said isopropyl alcohol after grinding.

5. The method of claim 1 wherein said ground sample portion and said carrier are mixed in a proportion of about 1 to 3 parts of ground sample portion to about 1000 parts of carrier by weight.

6. The method of claim 1 wherein said carrier is potassium bromide.

7. The method of claim 1 including the additional step of drying the mixture of said ground sample portion and said carrier before pressing said mixture into a thin wafer.

8. The method of claim 7 wherein said drying is carried out in an oven at about 65° C.

9. The method of claim 1 wherein said sample spectral response is obtained in wavelength range of from about 2 microns to about 25 microns.

10. The method of claim 1 wherein step (f) comprises smoothing the spectral response and interrogating the smoothed response over the range of about 5000 wave numbers to about 400 wave numbers to determine the wave number location and amplitude of the spectral peaks.

11. A method for determining the mineral composition of core sample obtained from a borehole in the earth wherein said sample has been cleaned to remove entrapped hydrocarbons, said method comprising the steps of:
   (a) coarse grinding said sample until no particles in excess of 0.5 millimeter remain;
   (b) further grinding said coarsely ground sample until the average particle size is less than about 1.0 micron with no particles larger than about 2.0 micron;

(c) drying said ground sample;
(d) mixing about 1 to 3 parts of said ground sample with about 1000 parts of potassium bromide;
(e) pressing about 200 milligrams of the mixture obtained in step (d) into a relatively thin wafer;
(f) subjecting said thin wafer to infra-red energy in a Fourier transform infra-red spectrometer and observing the resulting spectral response in the region of 5000 wave numbers to 400 wave numbers; and
(g) comparing said observed spectral response with the spectral responses of known standard minerals in a digital computer to determine the quantitative mineral composition of said core sample.

12. The method of claim 11 including the additional step of drying the mixture obtained in step (d) at about 65° C. for about 10 minutes before performing step (e).

13. A process for quantitative mineral analysis of a sample taken from a borehole in the earth comprising the steps of:

(a) cleaning said sample to remove any hydrocarbons;
(b) grinding said sample to reduce the average particle size to less than 1 micron with no particles greater than 2 microns;
(c) drying said ground sample;
(d) mixing a quantity of said sample with a quantity of potassium bromide;
(e) heating the mixture obtained in step (d) to evaporate moisture;
(f) pressing at least a portion of said mixture to obtain a thin wafer;
(g) examining said wafer in a Fourier transform infra-red spectrometer;
(h) collecting the infra-red responses of said, wafer in the 5000–400 wave number range;
(i) comparing the responses collected in step (h) with known responses of pure standard minerals in a digital computer to determine the quantitative mineral composition of said sample.

* * * * *